(12) United States Patent
Park et al.

(10) Patent No.: US 10,182,749 B2
(45) Date of Patent: Jan. 22, 2019

(54) HEALTH CARE APPARATUS AND OPERATING METHOD THEREOF

(71) Applicant: SAMSUNG ELECTRONICS CO., LTD., Suwon-si (KR)

(72) Inventors: Jinyoung Park, Hwaseong-si (KR); Eunsung Park, Seongnam-si (KR); Seongho Cho, Gwacheon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 678 days.

(21) Appl. No.: 14/835,022

(22) Filed: Aug. 25, 2015

(65) Prior Publication Data
US 2016/0213290 A1   Jul. 28, 2016

(30) Foreign Application Priority Data

Jan. 22, 2015   (KR) .................. 10-2015-0010548

(51) Int. Cl.
*A61B 5/00* (2006.01)
*A61B 5/145* (2006.01)
*A61B 5/1455* (2006.01)

(52) U.S. Cl.
CPC ........ *A61B 5/14532* (2013.01); *A61B 5/1455* (2013.01); *A61B 5/681* (2013.01)

(58) Field of Classification Search
CPC ... A61B 5/0205; A61B 5/0059; A61B 5/1455; A61B 5/14532; A61B 5/742; A61B 5/681
See application file for complete search history.

(56) References Cited

U.S. PATENT DOCUMENTS

| | | | |
|---|---|---|---|
| 6,070,093 A * | 5/2000 | Oosta | A61B 5/0095 356/39 |
| 8,568,820 B2 | 10/2013 | Zirkia | |
| 2003/0017191 A1* | 1/2003 | Wolf | A61K 31/70 424/439 |
| 2005/0175674 A1* | 8/2005 | Lang | A61K 31/353 424/442 |
| 2010/0075353 A1 | 3/2010 | Heaton | |
| 2010/0216098 A1 | 8/2010 | Montgomery | |
| 2011/0009720 A1 | 1/2011 | Kunjan et al. | |
| 2011/0053121 A1 | 3/2011 | Heaton | |
| 2011/0082711 A1 | 4/2011 | Poeze et al. | |
| 2013/0096842 A1 | 4/2013 | Sato et al. | |

(Continued)

FOREIGN PATENT DOCUMENTS

| | | |
|---|---|---|
| JP | 201245191 A | 3/2012 |
| KR | 1020130028415 A | 3/2013 |

*Primary Examiner* — Eric Winakur
*Assistant Examiner* — Chu Chuan (JJ) Liu
(74) *Attorney, Agent, or Firm* — Sughrue Mion, PLLC (57) ABSTRACT

A health care apparatus and an operating method thereof are provided. The method includes generating a first blood glucose pattern of an examinee that indicates a blood glucose level of the examinee over a first period of time, generating a second blood glucose pattern of the examinee that indicates the blood glucose level of the examinee over a second period of time, generating a third blood glucose pattern of the examinee that indicates the blood glucose level of the examinee over a third period of time, and calculating a glycemic index of the examinee based on the first blood glucose pattern, the second blood glucose pattern, and the third blood glucose pattern.

18 Claims, 10 Drawing Sheets

(56) References Cited

U.S. PATENT DOCUMENTS

| | | |
|---|---|---|
| 2013/0173339 A1 | 7/2013 | Briancon et al. |
| 2013/0187780 A1 | 7/2013 | Angelides |
| 2013/0217979 A1* | 8/2013 | Blackadar ............ A61B 5/0024 600/301 |
| 2016/0029966 A1* | 2/2016 | Salas-Boni ........ A61B 5/02055 600/347 |

* cited by examiner

HEALTH CARE APPARATUS AND OPERATING METHOD THEREOF

CROSS-REFERENCE TO RELATED APPLICATION

This application claims priority from Korean Patent Application No. 10-2015-0010548, filed on Jan. 22, 2015, in the Korean Intellectual Property Office, the disclosure of which is incorporated herein by reference in its entirety.

BACKGROUND

1. Field

Apparatuses and methods consistent with exemplary embodiments relate to a health care apparatus, and an operating method thereof.

2. Description of the Related Art

Diseases such as diabetes and high blood pressure are affected by meals ingested by individuals. Each person needs to maintain a diet suitable for one's physical constitution and current health state. To find which diet is suitable for one's health state, each person may search for a suitable diet by directly recording the content and amount of a current diet and monitoring a bio-signal. However, a method of directly recording the content of the current diet by each person may result in skipped data, and may increase burden and stress to each person due to recording.

As interest on health sharply increases and a rate of adult disease increases, demand and distribution of apparatuses for individually checking health, such as a blood glucose sensor, a blood pressure sensor, etc., increase. The apparatuses may need to detect a type of meal ingested by a person.

SUMMARY

Exemplary embodiments address at least the above disadvantages and other disadvantages not described above. Also, exemplary embodiments are not required to overcome the disadvantages described above, and may not overcome any of the problems described above.

Exemplary embodiments provide a health care apparatus, and an operating method thereof.

According to an aspect of an exemplary embodiment, there is provided a method of operating a health care apparatus, the method including generating a first blood glucose pattern of an examinee that indicates a blood glucose level of the examinee over a first period of time, generating a second blood glucose pattern of the examinee that indicates the blood glucose level of the examinee over a second period of time, generating a third blood glucose pattern of the examinee that indicates the blood glucose level of the examinee over a third period of time, and calculating a glycemic index of the examinee based on the first blood glucose pattern, the second blood glucose pattern, and the third blood glucose pattern.

The generating the first blood glucose pattern, the second blood glucose pattern, and the third blood glucose pattern may include detecting the blood glucose level in a non-invasive manner.

The detecting may include using at least one among Raman spectroscopy, infrared absorption spectroscopy, and a radio frequency analysis method.

The examinee may have an empty stomach during the first period of time.

The second period of time may be after the examinee ingests a first meal, and the third period of time may be after the examinee ingests a second meal.

The first meal may be a standard meal set by the examinee, and the second meal may be a current meal input by the examinee.

The first period of time, the second period of time, and the third period of time may have a same duration.

The duration may be less than or equal to 24 hours.

The calculating may include calculating a first blood glucose area by integrating a difference between the second blood glucose pattern and the first blood glucose pattern with respect to time, calculating a second blood glucose area by integrating a difference between the third blood glucose pattern and the first blood glucose pattern with respect to time, and calculating the glycemic index based on the first blood glucose area and the second blood glucose area.

The glycemic index may be a ratio of the second blood glucose area to the first blood glucose area.

The method may further include displaying the glycemic index.

The glycemic index may be displayed as at least one among a figure and a graph.

The method may further include detecting biomedical information other than the blood glucose level of the examinee, and calculating a degree of correlation between the glycemic index and the biomedical information.

The method may further include determining whether the degree of correlation is greater than or equal to a value and whether the glycemic index is within a range, and monitoring the biomedical information in response to the determining that the degree of correlation is greater than or equal to the value and that the glycemic index is within the range.

The method may further include determining an amount of exercise performed by the examinee, and calculating a degree of correlation between the glycemic index and the amount of exercise.

The method may further include determining whether the degree of correlation is greater than or equal to a value and whether the glycemic index is within a range, and instructing the examinee to exercise, in response to the determining that the degree of correlation is greater than or equal to the value and that the glycemic index is within the range.

According to an aspect of another exemplary embodiment, there is provided a health care apparatus including a processor configured to generate a first blood glucose pattern of an examinee that indicates a blood glucose level of the examinee over a first period of time, generate a second blood glucose pattern of the examinee that indicates the blood glucose level of the examinee over a second period of time, generate a third blood glucose pattern of the examinee that indicates the blood glucose level of the examinee over a third period of time, and calculate a glycemic index of the examinee based on the first blood glucose pattern, the second blood glucose pattern, and the third blood glucose pattern.

The apparatus may further include a sensor configured to detect the blood glucose level.

BRIEF DESCRIPTION OF THE DRAWINGS

The above and/or other aspects will be more apparent by describing in detail exemplary embodiments with reference to the accompanying drawings, in which.

DETAILED DESCRIPTION OF THE EXEMPLARY EMBODIMENTS

Hereinafter, exemplary embodiments are described in more detail with reference to the accompanying drawings.

In the following description, like reference numerals are used for like elements even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail because they would obscure the exemplary embodiments with unnecessary detail.

It will be understood that the terms such as "unit," "-er (-or)," and "module" described in the specification refer to an element configured to perform at least one function or operation, and may be implemented in hardware or a combination of hardware and software. When a constituent element "connects" or is "connected" to another constituent element, the constituent element contacts or is connected to the other constituent element not only directly but also electrically through at least one of other constituent elements interposed therebetween.

According to an exemplary embodiment, a health care apparatus may be an apparatus that may be carried by a user, for example, a wearable apparatus. The health care apparatus may be any one of apparatuses of a wristwatch type, a bracelet type, a ring type, a hairband type, etc., having a communication function and a data processing function, or a combination of two types. However, in exemplary embodiments, although the health care apparatus is assumed to be an apparatus of a wristwatch type or a hand-band type, the exemplary embodiments are not limited thereto.

Also, the health care apparatus may be embodied by a single housing or a plurality of housings. When the health care apparatus is embodied by a plurality of housings, a plurality of constituent elements may be connected by wire or wirelessly. For example, the health care apparatus may be divided into a first apparatus including a sensor for detecting biomedical information by being worn on a user's wrist and a second apparatus for processing the biomedical information. The health care apparatus may be embodied by some parts of an apparatus for performing other functions, for example, a mobile terminal.

Figure 1A:
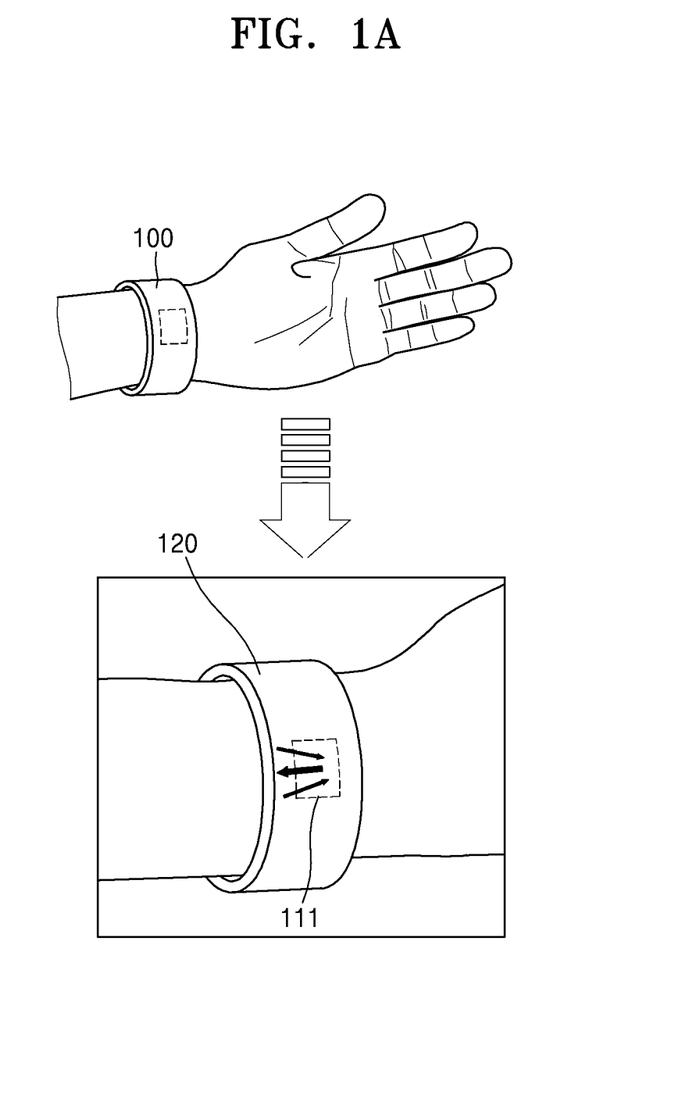
FIGS. 1A and 1B are diagrams of a health care apparatus worn on a wrist according to exemplary embodiments.
Figure 1B:
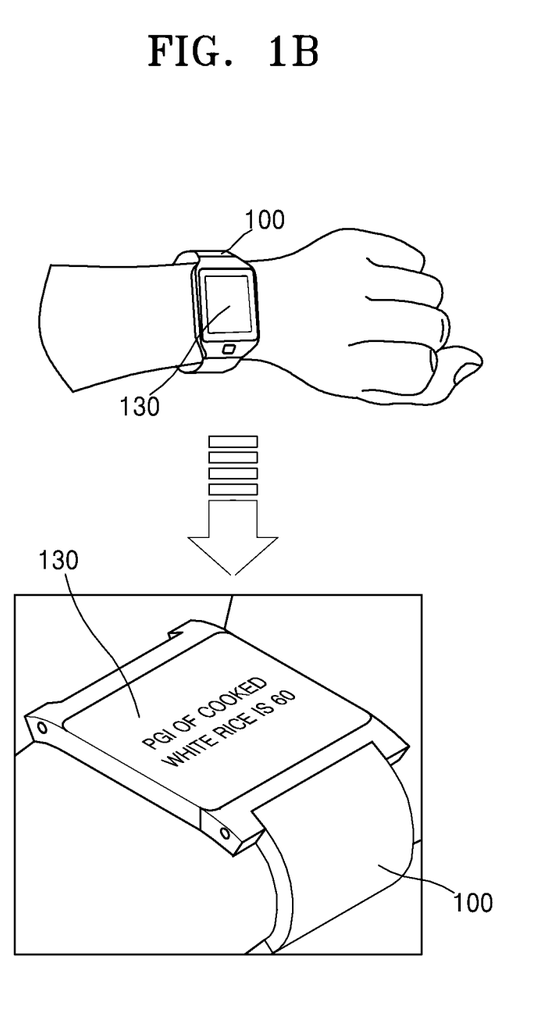

FIGS. 1A and 1B are diagrams of a health care apparatus 100 worn on a wrist according to exemplary embodiments. Referring to FIG. 1A, the health care apparatus 100 includes a first sensor 111 for detecting blood glucose through a user's wrist in a state of being worn on the wrist. Also, the health care apparatus 100 includes a processor 120 for processing blood glucose. The processor 120 may calculate a personalized glycemic index (PGI) from the blood glucose received from the first sensor 111.

Referring to FIG. 1B, the user receives the personalized glycemic index calculated by the processor 120 through a screen displayed on a display 130 of the health care apparatus 100 worn on the wrist. In addition, the health care apparatus 100 may monitor a health state of the user or guide exercise of the user based on the personalized glycemic index.

Figure 2:
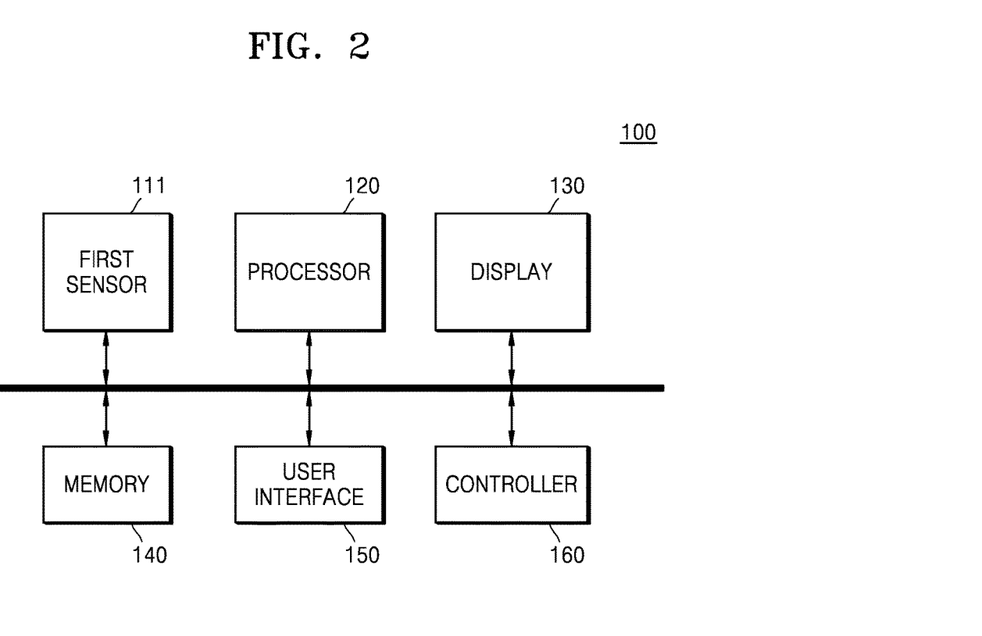
FIG. 2 is a block diagram of the health care apparatus of FIGS. 1A and 1B.

FIG. 2 is a block diagram of the health care apparatus 100 of FIGS. 1A and 1B. Referring to FIG. 2, the health care apparatus 100 includes the first sensor 111 for detecting blood glucose of an examinee, the processor 120 for calculating a personalized glycemic index of the examinee by using the blood glucose detected by the first sensor 111, and the display 130 for displaying the personalized glycemic index and information related to the personalized glycemic index. The health care apparatus further includes a memory 140 for storing a program that may be used for the health care apparatus 100, a user interface 150 for receiving an input of a user's command, and a controller 160 for controlling constituent elements of the health care apparatus 100.

The first sensor 111 detects blood glucose from blood of the examinee. The first sensor 111 may detect blood glucose in a non-invasive method. For example, the first sensor 111 may measure blood glucose of the examinee based on a reaction to light of blood or tissues included in the examinee. The first sensor 111 may use Raman spectroscopy, infrared absorption spectroscopy, or an RF analysis method. A molecule included in the blood or tissues of an examinee may absorb a light beam having a particular wavelength according to a bonding structure of the molecule, a shape of the molecule, potential energy surface (PES), masses of atoms, vibration coupling, etc. Accordingly, the blood glucose of the examinee may be measured by analyzing transmittance or absorbance of a wavelength absorbed by glucose, on a spectrum of a patient.

When the examinee ingests meal, a state of the examinee changes. For example, as the examinee ingests meal, viscosity of blood, a flow of heat accompanying digestion, particularity of blood ingredients, transparency, etc. are changed. Blood glucose ingested by the examinee may be detected by detecting the state of the examinee. When blood glucose ingested by the examinee is anticipated by detecting other ingredients instead of directly detecting meal ingredients in blood, a database containing degrees of correlation between meal and detected information may be used.

The first sensor 111 may be worn on, for example, the wrist, chest, or ankle of a user. The examinee is an object that ingests meal and has biomedical information varying according thereto. The examinee may include a human or animal, or part of a human or animal.

The processor 120 calculates a blood glucose pattern of the examinee by using the detected blood glucose. The blood glucose pattern may be a function indicating a change of the blood glucose according to time. Also, the processor 120 may calculate the personalized glycemic index by using the blood glucose pattern and a degree of correlation between the personalized glycemic index and the health state of the examinee. In addition, the processor 120 may calculate a degree of correlation between exercise and a change of the personalized glycemic index.

The display 130 displays information processed by the health care apparatus 100. For example, the display 130 may display a user interface (UI) or a graphical user interface personalized (GUI) to display a glycemic index, etc. The personalized glycemic index may be indicated by at least one of a number and a graph. The display 130 may include at least one of liquid crystal displays, thin film transistor-liquid crystal displays, organic light-emitting diodes, flexible displays, 3D displays, etc. Two or more displays 130 may exist according to an implementation form of the health care apparatus 100.

The display 130 may constitute a touch screen by forming a mutual layer structure with a touch pad for receiving an input of a user. When the display 130 constitutes a touch screen by forming a mutual layer structure with a touch pad, the display 130 may be used not only as an output device but also as an input device. The display 130 formed as a touch screen may automatically initiate measurement of a biomedical signal as the display 130 detects a user's touch input in a predetermined area.

The memory 140 stores data generated during an operation of the health care apparatus 100. The memory 140 may include any of hard disk drives (HDDs), read only memory (ROM), random access memory (RAM), flash memory, and memory cards, as a typical storage medium, which is well-known to one of ordinary skill in the art.

The user interface 150 may receive an input to manipulate the health care apparatus 100 from the user, or output at least one of the personalized glycemic index and first and second degrees of correlation, processed by the health care apparatus 100. The user interface 150 may include at least one of a button, a keypad, a switch, a dial, and a touch interface so that the user may directly manipulate the health care apparatus 100. The user interface 150 may include a display for displaying an image, which may be embodied as a touch screen. The user interface 150 may include an I/O port to connect human interface devices (HIDs). The user interface 150 may include an I/O port for input/output of an image.

The controller 160 controls an overall operation of the health care apparatus 100. For example, the controller 160 may control the first sensor 111 to detect blood glucose. Also, the controller 160 may determine whether the examinee excessively ingests meal by analyzing the detected blood glucose and blood glucose pattern, and may provide the user with a result of the analysis through the display 130.

Figure 3:
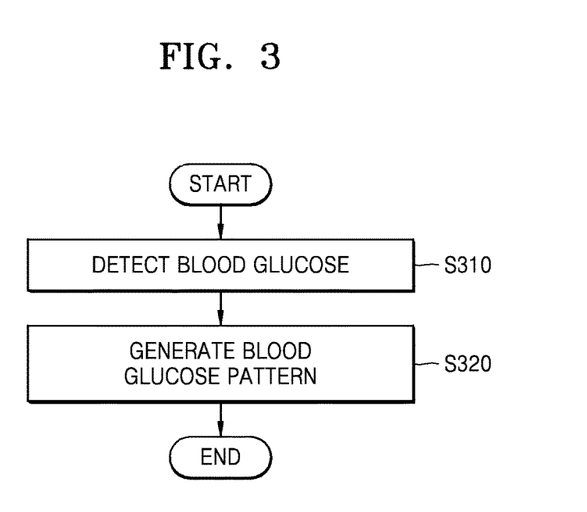
FIG. 3 is a flowchart of a method in which a health care apparatus generates a blood glucose pattern, according to an exemplary embodiment.

FIG. 3 is a flowchart of a method in which the health care apparatus 100 generates a blood glucose pattern, according to an exemplary embodiment. Referring to FIG. 3, the first sensor 111 detects blood glucose (S310). The first sensor 111 may detect blood glucose ingested by the examinee from the examinee in a non-invasive method by using light. For example, the first sensor 111 may detect blood glucose by using Raman spectroscopy, infrared absorption spectroscopy, or an RF analysis method. This is because a light absorption wavelength varies according to a molecular structure of saccharide.

The processor 120 calculates a blood glucose pattern of an examinee according to time by using the blood glucose detected by the first sensor 111 (S320). The blood glucose pattern may be a function indicating a change of blood glucose according to time.

Alternatively, a degree of increasing concentration of glucose in blood is various according to a type of meal. In this regard, a concept of "glycemic index" has been introduced. The glycemic index is an index objectively indicating an effect of carbohydrate in ingested meal on blood glucose. To calculate the glycemic index, a plurality of healthy adults, for example, 8 to 9 persons, ingests meal containing 50 g of standard meal, for example, glucose. Then, a change of blood glucose occurs for a predetermined time, for example, 2 to 3 hours. A glycemic index of the standard meal is calculated by repeating the above measurement.

However, the glycemic index has some problems. First, because a degree of response to insulin varies person to person, even when the same meal is ingested, a change of blood glucose being measured may vary. Second, for the same type of meal, a change of blood glucose may vary according to the place of origin or a manufacturing method. Third, even when the same person ingests the same meal, a change of blood glucose may be generated according to the state of person when the meal is ingested. Fourth, because the glycemic index takes only about two hours after ingesting a meal into consideration, the glycemic index may not be data suitable for an examinee such as a glucose tolerant patient or a diabetes patient. Fifth, because the glycemic index is a figure about individually ingested meal, it may be difficult to provide an accurate glycemic index for a user taking a plurality of meals.

The health care apparatus 100 may calculate a personalized glycemic index of the examinee, that is, each individual, by using a blood glucose pattern acquired from each individual. Prior to the calculation of a glycemic index, the health care apparatus 100 may calculate a blood glucose area.

Figure 4:
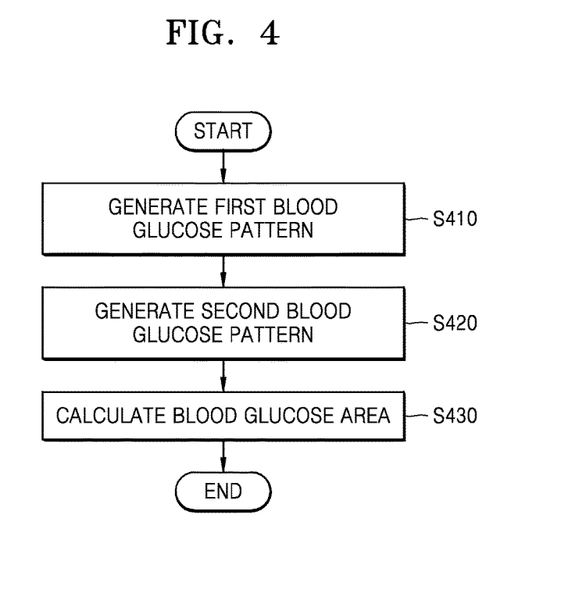
FIG. 4 is a flowchart of a method of calculating a blood glucose area by using a blood glucose pattern, according to an exemplary embodiment.

FIG. 4 is a flowchart of a method of calculating a blood glucose area by using a blood glucose pattern, according to an exemplary embodiment. Referring to FIG. 4, the health care apparatus 100 generates a first blood glucose pattern by detecting blood glucose from the examinee for a first time period (S410). During the first time period, the first sensor 111 may detect blood glucose from blood of the examinee, and the processor 120 may generate a first blood glucose pattern that is a function according to time, based on the blood glucose detected during the first time period. The examinee may be on an empty stomach during the first time period. The first time period may be 24 hours. For example, the first time period may be from 0 o'clock to 24 o'clock. Alternatively, the first time period may be from 2 o'clock to 3 o'clock. For example, the first time period may be from 12 o'clock to 14 o'clock.

The health care apparatus 100 generates a second blood glucose pattern by detecting the blood glucose from the examinee for a second time period (S420). For example, the first sensor 111 may detect blood glucose from blood of the examinee during the second time period, and the processor 120 may generate a second blood glucose pattern that is a function according to time, based on the blood glucose detected during the second time period.

The second time period may have the same duration as the above-described first time period, but have different starting points. For example, the first time period may be from 0 o'clock to 24 o'clock of Dec. 1, 2014, whereas the second time period may be from 0 o'clock to 24 o'clock of Dec. 10, 2014. Alternatively, the first time period may be from 12 o'clock to 14 o'clock of Dec. 1, 2014, whereas the second time period may be from 12 o'clock to 14 o'clock of Dec. 10, 2014. The examinee may ingest a meal during the second time period. Alternatively, the examinee may ingest a meal at a start time point of the second time period or finish the ingestion at the start time point of the second time period. Also, the second time period may be a time regardless of whether the examinee ingests a meal. The first time period and the second time period may be set by the examinee.

The processor 120 calculates a blood glucose area by using the first blood glucose pattern and the second blood glucose pattern (S430). The blood glucose area may be obtained by integrating a difference between the second blood glucose pattern and the first blood glucose pattern with respect to time. For example, the blood glucose area may be a value obtained by integrating positive values of values obtained by subtracting the first blood glucose pattern from the second blood glucose pattern.

Figure 5:
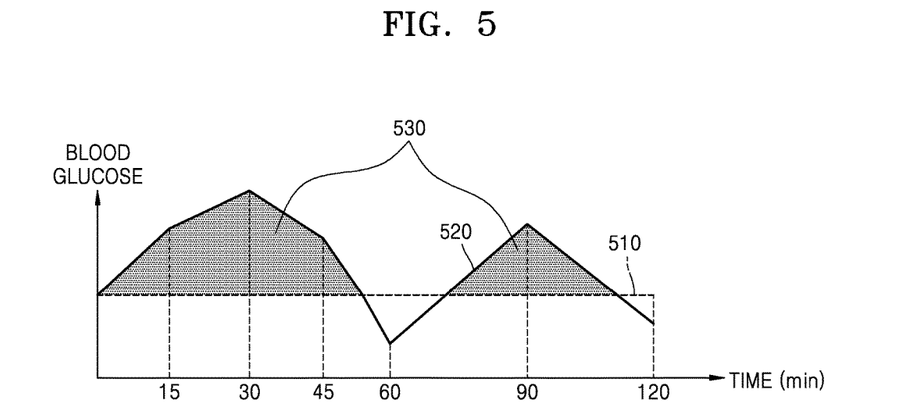
FIG. 5 is a graph illustrating a method of calculating a blood glucose area, according to an exemplary embodiment.

FIG. 5 is a graph illustrating a method of calculating a blood glucose area, according to an exemplary embodiment. As illustrated in FIG. 5, the processor 120 generates a first blood glucose pattern 510 for two hours on an empty stomach and a second blood glucose pattern 520 for two hours after taking a meal. The processor 120 calculates a blood glucose area 530 by integrating positive values of values obtained by subtracting the first blood glucose pattern 510 from the second blood glucose pattern 520. The health care apparatus 100 may calculate a personalized glycemic index by using the blood glucose area.

Figure 6:
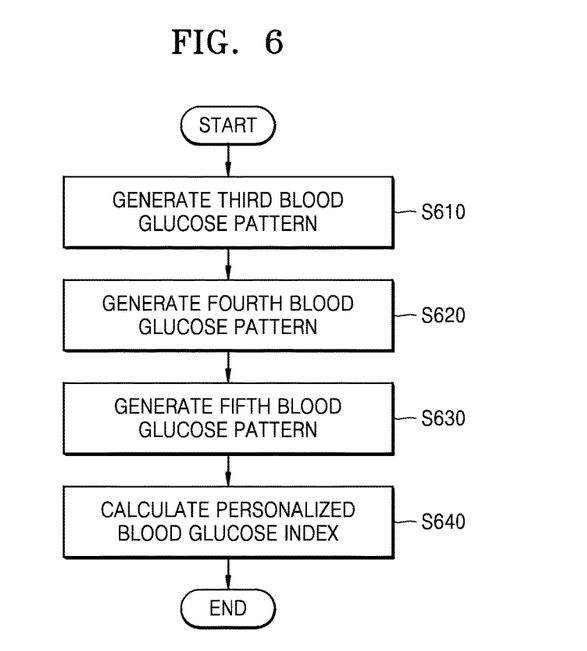
FIG. 6 is a flowchart of a method of calculating a personalized glycemic index, according to an exemplary embodiment.

FIG. 6 is a flowchart of a method of calculating a personalized glycemic index, according to an exemplary embodiment. Referring to FIG. 6, the health care apparatus 100 generates a third blood glucose pattern by detecting blood glucose from the examinee for a third time period (S610). During the third time period, the first sensor 111 may detect blood glucose from the examinee, and the processor 120 may generate a third blood glucose pattern according to time, based on the blood glucose detected during the third time period.

The examinee may be on an empty stomach during the third time period. The third time period may be 24 hours. For example, the third time period may be from 0 o'clock to 24 o'clock. Alternatively, the third time period may be from 2 o'clock to 3 o'clock. For example, the third time period may be from 12 o'clock to 14 o'clock.

The health care apparatus 100 generates a fourth blood glucose pattern by detecting blood glucose from the examinee for a fourth time period (S620). For example, for the fourth time period, the first sensor 111 may detect blood glucose from the examinee, and the processor 120 may generate a fourth blood glucose pattern that is a function according to time, based on the blood glucose detected for the fourth time period.

The fourth time period may have the same duration as the above-described third time period, but have different starting points. For example, the third time period may be from 0 o'clock to 24 o'clock of Dec. 1, 2014, whereas the fourth time period may be from 0 o'clock to 24 o'clock of Dec. 10, 2014. Alternatively, the third time period may be from 12 o'clock to 14 o'clock of Dec. 1, 2014, whereas the fourth time period may be from 12 o'clock to 14 o'clock of Dec. 10, 2014.

The examinee may ingest a meal during the fourth time period. Alternatively, the examinee may ingest a meal at a start time point of the fourth time period or finish the ingestion at the start time point of the fourth time period. The meal may be a standard meal. The standard meal may be meal used as a standard for calculating the personalized glycemic index. The standard meal may be one meal or one-day meal of the examinee. The standard meal may be freely set by the examinee or the user, and may be one meal or one-day meal recommended by a medical society.

The health care apparatus 100 generates a fifth blood glucose pattern by detecting blood glucose from the examinee for a fifth time period (S630). For example, for the fifth time period, the first sensor 111 may detect blood glucose from the examinee, and the processor 120 may generate a fifth blood glucose pattern that is a function according to time, based on the blood glucose detected for the fifth time period.

The fifth time period may have the same duration as the above-described second and third time periods but different starting points. For example, the fifth time period may be from 0 o'clock to 24 o'clock of Dec. 12, 2014, or from 12 o'clock to 14 o'clock of Dec. 12, 2014.

The examinee may ingest a meal during the fifth time period. Alternatively, the examinee may ingest a meal at a start time point of the fifth time period or finish the ingestion at the start time point of the fifth time period. The meal may be freely ingested by the examinee. The health care apparatus 100 compares the blood glucose of the meal ingested by the examinee for the fifth time period and the blood glucose of the standard meal.

The health care apparatus 100 generates a personalized glycemic index by using the third to fifth blood glucose patterns (S640). The processor 120 may calculate a first blood glucose area by using the third blood glucose pattern and the fourth blood glucose pattern, and a second blood glucose area by using the third blood glucose pattern and the fifth blood glucose pattern. As described above, the blood glucose area may be a value obtained by integrating a difference between the blood glucose patterns with respect to time. For example, the first blood glucose area may be a value obtained by integrating positive values of values obtained by subtracting the third blood glucose pattern from the fourth blood glucose pattern with respect to time, and the second blood glucose area may be a value obtained by integrating positive values of values obtained by subtracting the fourth blood glucose pattern from the fifth blood glucose pattern with respect to time.

The processor 120 may calculate a personalized glycemic index by using the first blood glucose area and the second blood glucose area. The personalized glycemic index may include the second blood glucose area with respect to the first blood glucose area. For example, the personalized glycemic index may be a value obtained by multiplying a ratio of the second blood glucose area to the first blood glucose area by 100.

Figure 7A:
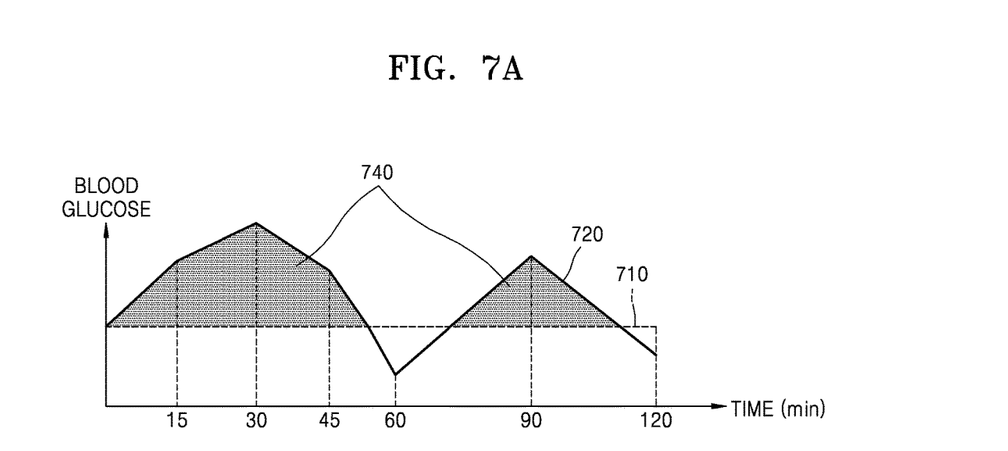
FIGS. 7A and 7B are graphs illustrating a method of calculating a personalized glycemic index, according to an exemplary embodiment.
Figure 7B:
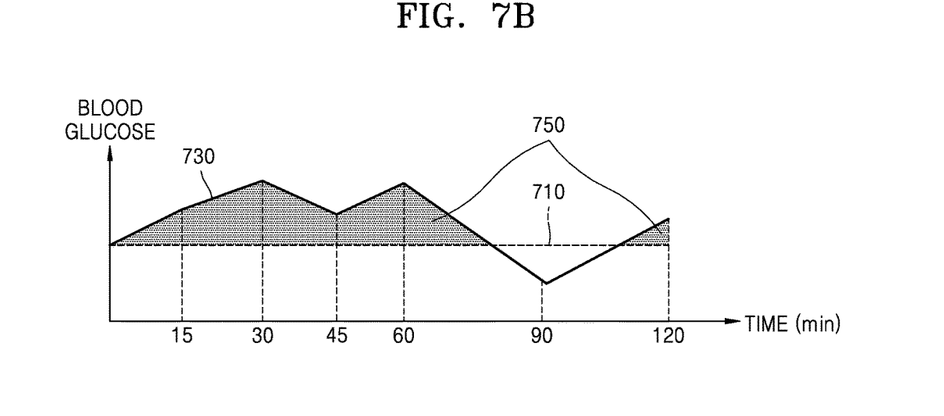

FIGS. 7A and 7B are graphs illustrating a method of calculating a personalized glycemic index, according to an exemplary embodiment. As illustrated in FIG. 7A, the processor 120 generates a third blood glucose pattern 710 on an empty stomach and a fourth blood glucose pattern 720 for two hours after taking the standard meal. Also, as illustrated in FIG. 7B, the processor 120 may generate a fifth blood glucose pattern 730 for two hours after freely ingesting a meal. The processor 120 may calculate a first blood glucose area 740 by integrating a positive value obtained by subtracting the third blood glucose pattern 710 from the fourth blood glucose pattern 720 in FIG. 7A with respect to time. The processor 120 may calculate a second blood glucose area 750 by integrating a positive value obtained by subtracting the third blood glucose pattern 710 from the fifth blood glucose pattern 730 in FIG. 7B with respect to time. The processor 120 may calculate a value obtained by multiplying a ratio of the second blood glucose area 750 with respect to the first blood glucose area 740 by 100 as a personalized glycemic index.

As such, because the personalized glycemic index is calculated by using the blood glucose detected from the examinee, the examinee may conveniently determine meal that is suitable for one's health. Because the personalized glycemic index is calculated for each meal, the user may easily obtain a personalized glycemic index for each meal.

Figure 8A:
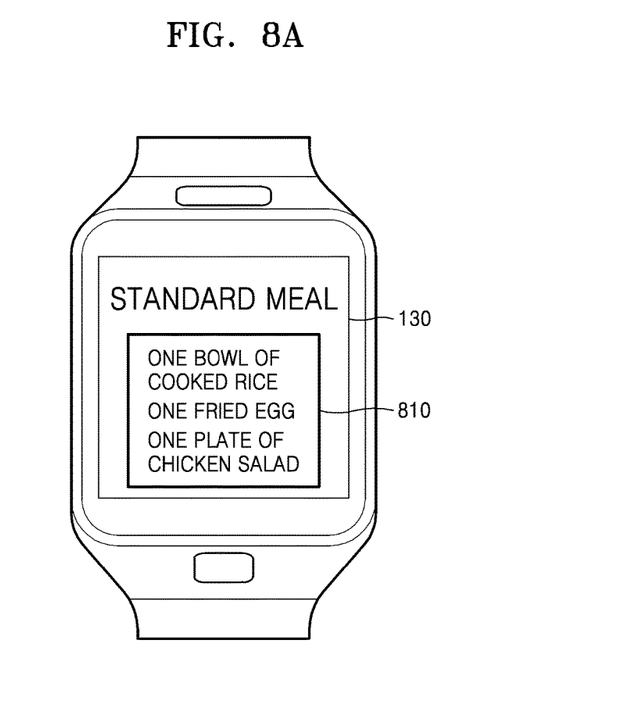
FIGS. 8A to 8C are reference diagrams illustrating a method of calculating a personalized glycemic index accordingly to an exemplary embodiment.
Figure 8B:
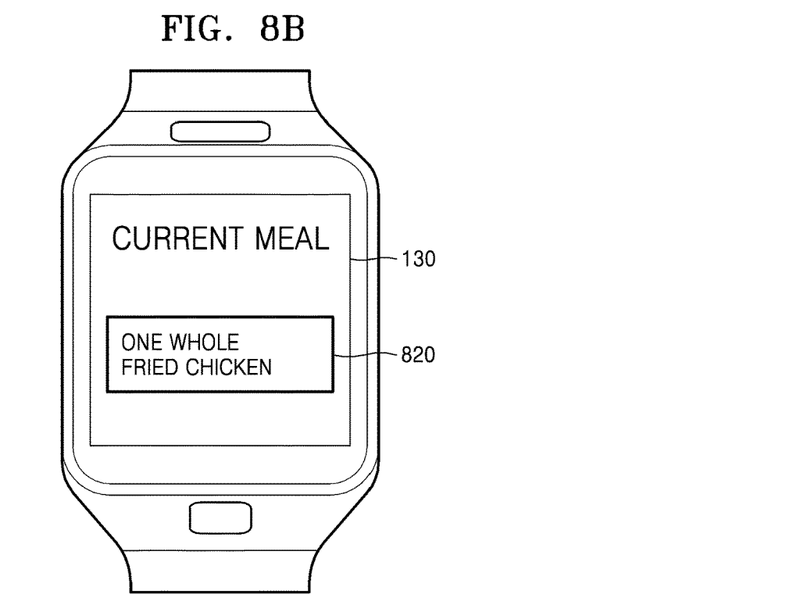
Figure 8C:
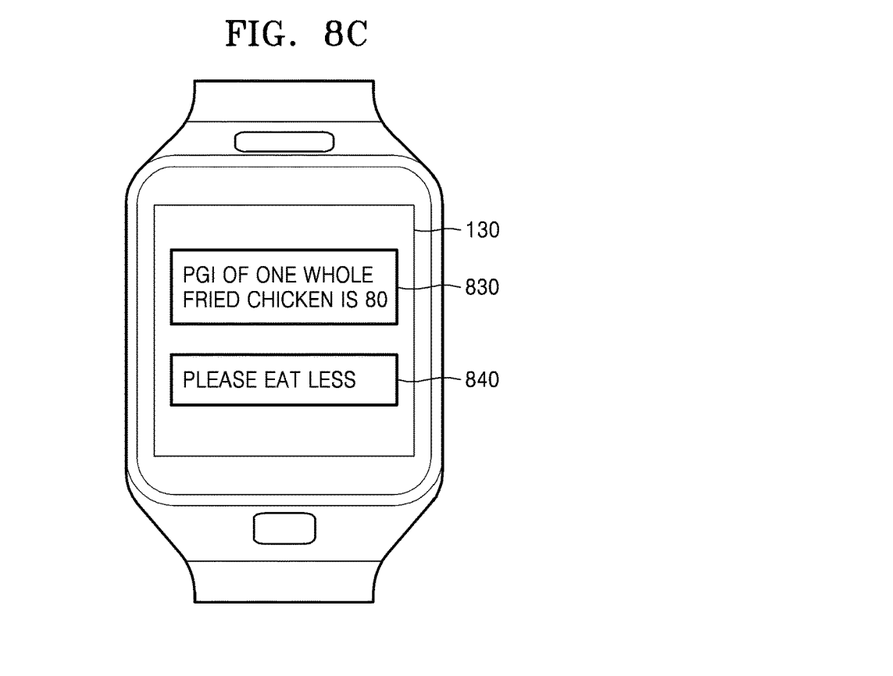

FIGS. 8A to 8C are reference diagrams illustrating a method of calculating a personalized glycemic index according to an exemplary embodiment. After setting a mode of the health care apparatus 100 to a personalized glycemic index calculation mode, the examinee may input meal information 810 about the standard meal. For example, as illustrated in FIG. 8A, the examinee inputs one bowl of cooked rice, one fried egg, one plate of chicken salad, as the information 810 about the standard meal. The examinee may ingest the standard meal after activating the first sensor 111.

The health care apparatus 100 may detect blood glucose. The first sensor 111 may detect blood glucose for three hours at a predetermined time interval, for example, every 15 minutes. Alternatively, the first sensor 111 may detect blood glucose at an interval of 15 minutes for the first hour from a meal taking start time and then at an interval of 30 minutes for the next two hours. The processor 120 may generate a standard blood glucose pattern from the detected blood glucose. The standard blood glucose pattern signifies a blood glucose pattern according to the standard meal. The processor 120 may calculate a standard blood glucose area by using the standard blood glucose pattern and the blood glucose pattern on an empty stomach.

Also, as illustrated in FIG. 8B, the examinee inputs one whole fried chicken as information 820 about a target meal or current meal to find out a personalized glycemic index thereof. The examinee may ingest the target meal after activating the first sensor 111. The health care apparatus 100 may detect blood glucose. The first sensor 111 may detect blood glucose about the target meal in the same method as the method of detecting blood glucose with respect to the target meal. The processor 120 may generate a target blood glucose pattern from the detected blood glucose.

The processor 120 may calculate a target blood glucose area by using the target blood glucose pattern and the blood glucose pattern on an empty stomach. The target blood glucose pattern signifies a blood glucose pattern according to the target meal.

Also, the processor 120 may calculate a personalized glycemic index with respect to the target meal by multiplying a ratio of the target blood glucose area with respect to the standard blood glucose area by 100. The health care apparatus 100, as illustrated in FIG. 8C, displays a personalized glycemic index 830. Additionally, the health care apparatus 100 provides an evaluation 840 about the personalized glycemic index.

For example, when the personalized glycemic index is equal to or less than 40, the personalized glycemic index may be evaluated to low; when the personalized glycemic index is over 40 and less than 70, the personalized glycemic index may be evaluated to be intermediate; and when personalized glycemic index exceeds 70, the personalized glycemic index may be evaluated to be high. Thus, the health care apparatus 100 may provide evaluation of the personalized glycemic index of a target meal.

As described above, the health care apparatus 100 may create a database containing personalized glycemic indexes for each meal. Accordingly, the personalized glycemic index may be anticipated as the user inputs meal to ingest before having a meal, the user may control meal accordingly. In addition, even when the user does not input information about meal, the health care apparatus 100 may calculate the personalized glycemic index by detecting blood glucose. The health care apparatus 100 may calculate the personalized glycemic index in units of 2 hours, 4 hours, or 24 hours, and the calculated personalized glycemic index may be displayed by a figure or a graph. When the personalized glycemic index is too low or too high, the health care apparatus 100 may provide a guide to the meal control.

Alternatively, the blood glucose may have an influence on biomedical information about the examinee. Accordingly, the health care apparatus 100 may calculate a degree of correlation between blood glucose and an examinee's health state, and may provide information thereof.

Figure 9:
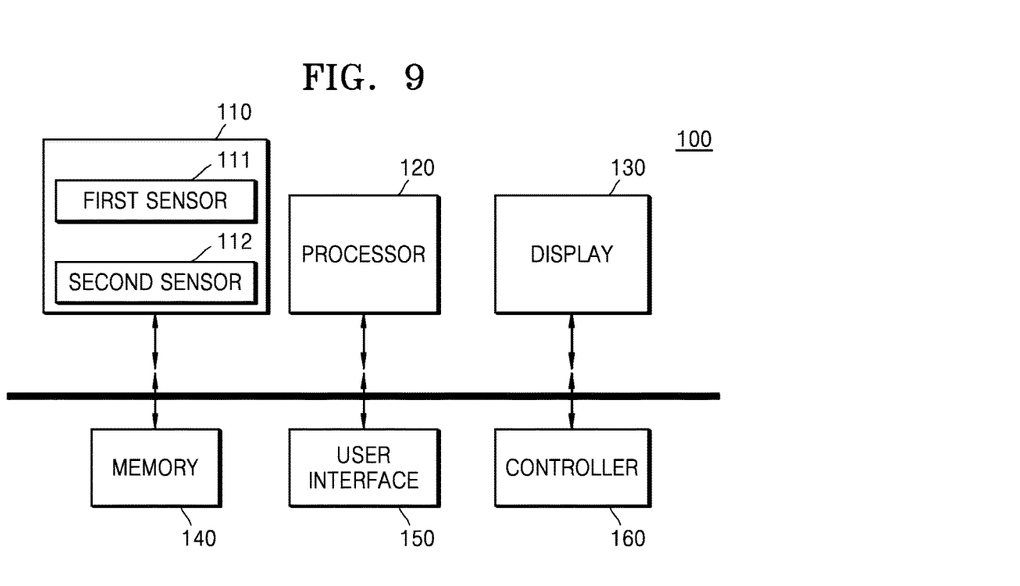
FIG. 9 is a block diagram of a health care apparatus according to another exemplary embodiment.

FIG. 9 is a block diagram of the health care apparatus 100 according to another exemplary embodiment. Referring to FIGS. 1 and 9, the health care apparatus 100 of FIG. 9 further includes a sensor 110 including the first sensor 111 and a second sensor 112 for detecting biomedical information of the examinee. Because the first sensor 111, the display 130, the memory 140, and the user interface 150 are the same as those described with reference to FIG. 1, detailed descriptions thereof are omitted.

The biomedical information may be an intrinsic signal generated from the examinee other than the blood glucose. For example, the biomedical information may be a signal according to a motion of an object, for example, a heart or muscle of the examinee, such as electrocardiogram (ECG), ballistocardiogram (BCG), photoplethysmograph (PPG), electromyogram, a blood pressure, etc., or information about a material included in the examinee, for example, an amount of cholesterol or body fat.

The second sensor 112 may detect biomedical information of the examinee in a non-invasive method. The second sensor 112 may include a plurality of electrodes that may contact the examinee when the examinee wears the second sensor 112. Thus, the second sensor 112 may detect biomedical information by measuring electrical properties, for example, a resistance change, according to a change of the biomedical information in blood. The second sensor 112 may detect biomedical information by using light in addition to the electrodes. Because the material included in the examinee has an intrinsic molecular structure, absorption wavelength ranges may vary.

The second sensor 112 may have a different detection method according to the type of biomedical information. For example, when the biomedical information is a signal according to a motion of an object, a sensor using electrical properties may be used. Also, when the information is about a material included in the examinee, a sensor using light may be used.

Also, the sensor 110 may include a motion sensor for detecting a motion of a user. The motion sensor may be an acceleration sensor, a gyro sensor, a terrestrial magnetic sensor, etc.

The processor 120 determines a health state from the detected biomedical information. The processor 120 may change the health state to an image or text. The processor 120 may use a different method of obtaining a health state according to the type of biomedical information. For example, when the biomedical information is body impedance, the processor 120 may obtain a body composition of a user by using body impedance. The body composition may be body fat, skin properties, for example, body water, muscle strength, existence of edema, skeletal muscle mass, muscle mass, a degree of obesity, body composition ratio, visceral fat amount, etc. Because the obtaining of a body composition from the body impedance is well-known, a detailed description thereof is omitted. Also, the processor 120 may obtain the body composition by referring to not only the body impedance but also user information. The user information may be information about age, weight, height, gender, etc. of a user.

Alternatively, when the biomedical information is an ECG signal according to the motion of a heart, the processor 120 may obtain a biomedical information waveform of from the biomedical information, and information about a health state such as the maximum blood pressure or minimum blood pressure, from the biomedical information waveform. When obtaining the biomedical information waveform, the processor 120 may amplify the ECG signal and filter the amplified ECG signal by using a FIR bandpass filter. A biomedical information waveform may be obtained by detecting a peak in the filtered ECG signal and adaptively filtering the detected peaks.

The processor 120 may calculate a degree of correlation between the personalized glycemic index and the biomedical information. The health state may be affected by the blood glucose. For example, the blood glucose may vary corresponding to the meal ingested by the examinee. Also, an effect of the blood glucose or a change in the blood glucose on health may vary according to examinees. For example, while a health state of an examinee may be sensitive to the personalized glycemic index, a health state of another examinee may be insensitive to the personalized glycemic index. Accordingly, the health care apparatus 100 may classify the biomedical information sensitive to the personalized glycemic index for each individual, and monitor a health state by using the personalized glycemic index.

Figure 10:
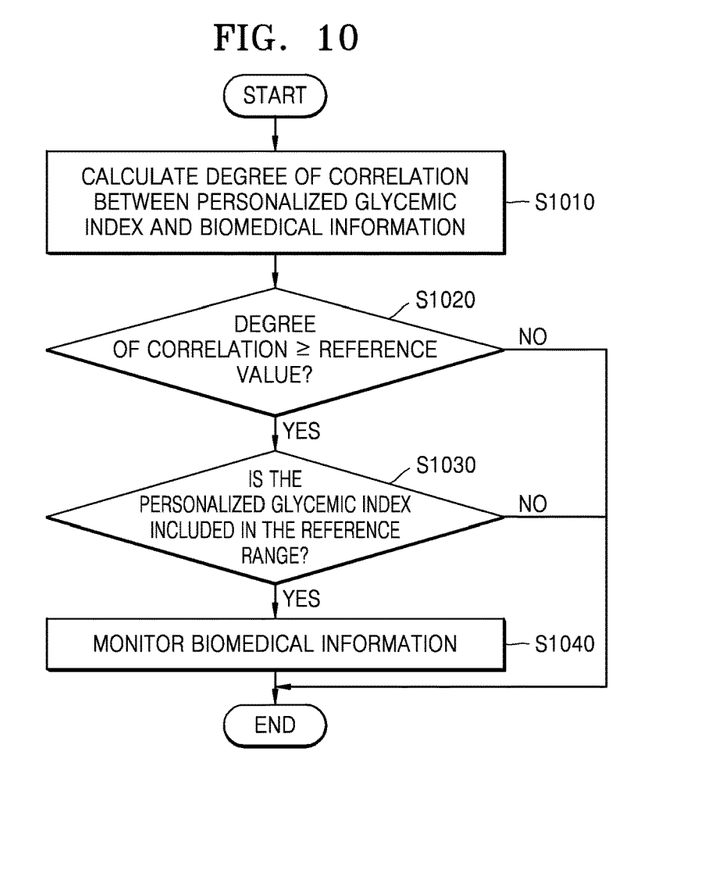
FIG. 10 is a flowchart of a method of using a degree of correlation between a personalized glycemic index and biomedical information, according to an exemplary embodiment.

FIG. 10 is a flowchart of a method of using a degree of correlation between a personalized glycemic index and biomedical information, according to an exemplary embodiment. Referring to FIG. 10, the health care apparatus 100, i.e., the processor 120, calculates a degree of correlation between the personalized glycemic index and the biomedical information (S1010). A health state may be determined from the biomedical information. Accordingly, the degree of correlation between the personalized glycemic index and the biomedical information may signify a degree of correlation between the personalized glycemic index and the health state. For example, the health care apparatus 100 may calculate a change of the glycemic index for a predetermined time, for example, 24 hours, and may detect a change of biomedical information for a predetermined time or a time slightly longer than the predetermined time, for example, 48 hours.

The health care apparatus 100 may create a database containing the calculated personalized glycemic indexes and biomedical information, and calculate a degree of correlation between the calculated personalized glycemic indexes and biomedical information. For example, even when the personalized glycemic index changes, if the biomedical information, for example, a heart rate, is constant, the personalized glycemic index and the heart rate may be determined to have no degree of correlation. Alternatively, when the change of a personalized glycemic index and the change of body impedance are proportional to each other, the health care apparatus 100 may determine that the personalized glycemic index and the body impedance have a degree of correlation. The degree of correlation may be calculated in a figure. For example, the health care apparatus 100 may calculate a degree of correlation from the absolute value with respect to the change of the biomedical information to the change of the personalized glycemic index. As the absolute value of a degree of the correlation increases, the change of the personalized glycemic index may have a great influence on the biomedical information.

The health care apparatus 100 determines whether the degree of correlation is greater than or equal to a reference value (S1020). When the degree of correlation is determined to be greater than or equal to the reference value (S1020—Yes), the health care apparatus 100 continues in operation S1030. Otherwise, the health care apparatus 100 ends operation.

The health care apparatus 100 determines whether the personalized glycemic index is included in a reference range (S1030). The reference range may be a range of the personalized glycemic index when the biomedical information is in an abnormal range. Alternatively, the reference range may be a range of the personalized glycemic index when the biomedical information is not only in the abnormal range, but also in a normal range that is likely to be the abnormal range. The memory 140 may previously store the reference range of the personalized glycemic index corresponding to each piece of the biomedical information. When the personalized glycemic index is determined to be included in the reference range (S1030—Yes), the health care apparatus 100 continues in operation S1040. Otherwise, the health care apparatus 100 ends operation.

The health care apparatus 100 monitors the biomedical information (S1040). The biomedical information may be biomedical information having a degree of correlation with the calculated personalized glycemic indexes that is equal to or more than the reference value. For example, when the degree of correlation between the personalized glycemic index and the minimum blood pressure is equal to or more than the reference value, and the personalized glycemic index is equal to or less than 40, the minimum blood pressure is highly likely to be included in an abnormal range. Thus, the health care apparatus 100 may monitor the minimum blood pressure when the personalized glycemic index is 38

In addition, the personalized glycemic index may be affected by a motion of the examinee. Even when the same meal is ingested, if the examinee moves much, the personalized glycemic index may be decreased. Accordingly, exercise may be guided according to the personalized glycemic index.

Figure 11:
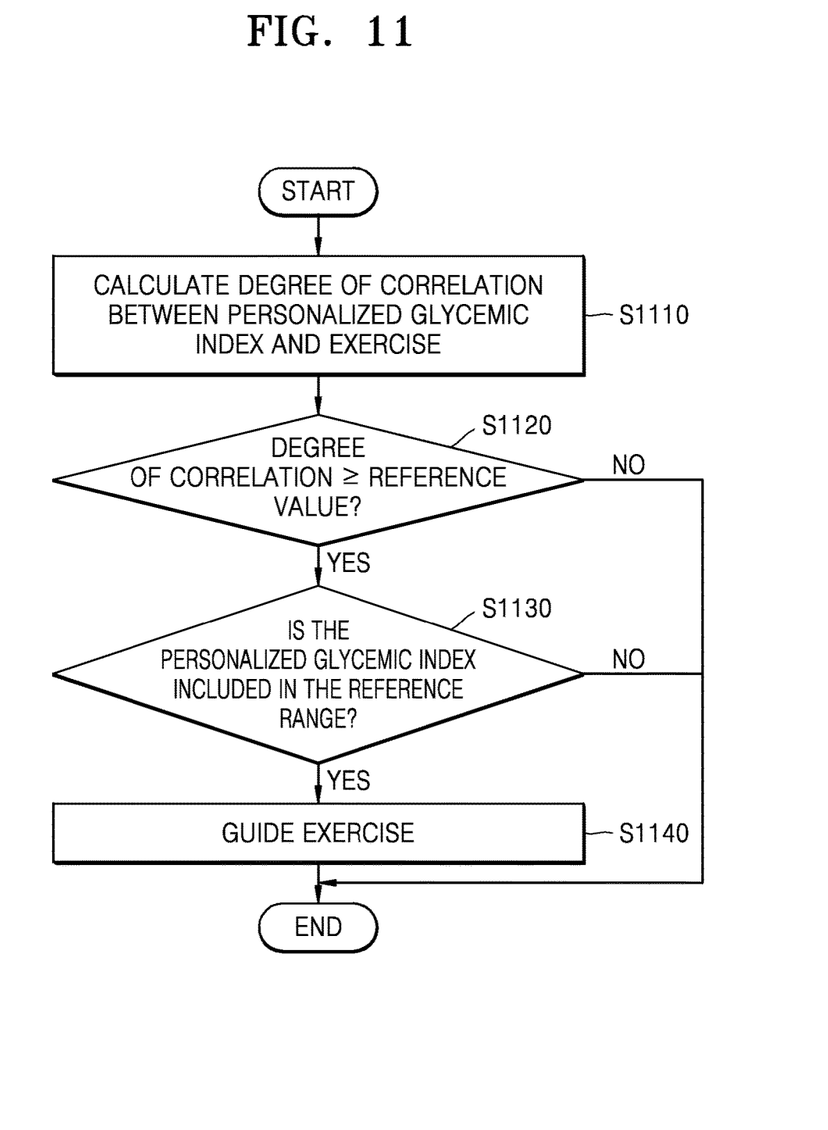
FIG. 11 is a flowchart of a method of using a degree of correlation between a personalized glycemic index and exercise, according to an exemplary embodiment.

FIG. 11 is a flowchart of a method of using a degree of correlation between a personalized glycemic index and exercise, according to an exemplary embodiment. Referring to FIG. 11, the health care apparatus 100, i.e., the processor 120, calculates a degree of correlation between the personalized glycemic index and exercise (S1110). For example, the health care apparatus 100 may calculate a change of a glycemic index for a predetermined time, for example, 24 hours, and detect an amount of exercise of the examinee for a predetermined time or a time slightly longer than the predetermined time. Alternatively, the health care apparatus 100 may calculate a change of the personalized glycemic index when the examinee exercises or does not exercise after taking the same meal. The health care apparatus 100 may calculate a degree of correlation between the personalized glycemic index and the exercise in a figure. For example, the health care apparatus 100 may define a degree of correlation by a change of the personalized glycemic index to a change of the amount of exercise.

The health care apparatus 100 determines whether the degree of correlation is greater than or equal to the reference value (S1120). A degree of influence of exercise on a change of the personalized glycemic index may vary for each individual. Only when the degree of correlation is equal to or more than the reference value, the health care apparatus 100 may guide exercise. When the degree of correlation is determined to be greater than or equal to the reference value (S1120—Yes), the health care apparatus 100 continues in operation S1130. Otherwise, the health care apparatus 100 ends operation.

The health care apparatus 100 determines whether the personalized glycemic index is included in the reference range (S1130). The reference range may be a range in which the personalized glycemic index is not only in an abnormal range, but also in a range that is likely to be the abnormal range. Also, a range in which the personalized glycemic index is in the abnormal range may be defined to be a range that may deteriorate health of the examinee. For example, when the personalized glycemic index is equal to or more than 90, the range may be an abnormal range. When the personalized glycemic index is determined to be included in the reference range (S1130—Yes), the health care apparatus 100 continues in operation S1140. Otherwise, the health care apparatus 100 ends operation.

The health care apparatus 100 guides exercise (S1140). The health care apparatus 100 may provide a guide to a type, amount, or method of exercise to have the personalized glycemic index escape from the reference range. For example, when the personalized glycemic index is equal to or more than 90, the health care apparatus 100 may provide a guide to the type, amount, or method of exercise to drop the personalized glycemic index down to 50.

In addition, environment information about external environment where the examinee is located and the personalized glycemic index may have a degree of correlation. The health care apparatus 100 may provide various pieces of information or action guidelines by using the degree of correlation.

As described above, the health care apparatus 100 may be embodied by a plurality of apparatuses. For example, the health care apparatus 100 may be embodied by a slave that detects the blood glucose, biomedical information, or motion of the examinee, and a master that calculates a personalized glycemic index from the detected blood glucose, calculates a degree of correlation with other biomedical information or exercise, and provides a result thereof. The slave and the master may be connected to each other in a wireless or wired communication. For example, the slave and the master may perform short range communication such as Bluetooth or WiFi, or communicate with each other through a mobile communication network.

Figure 12:
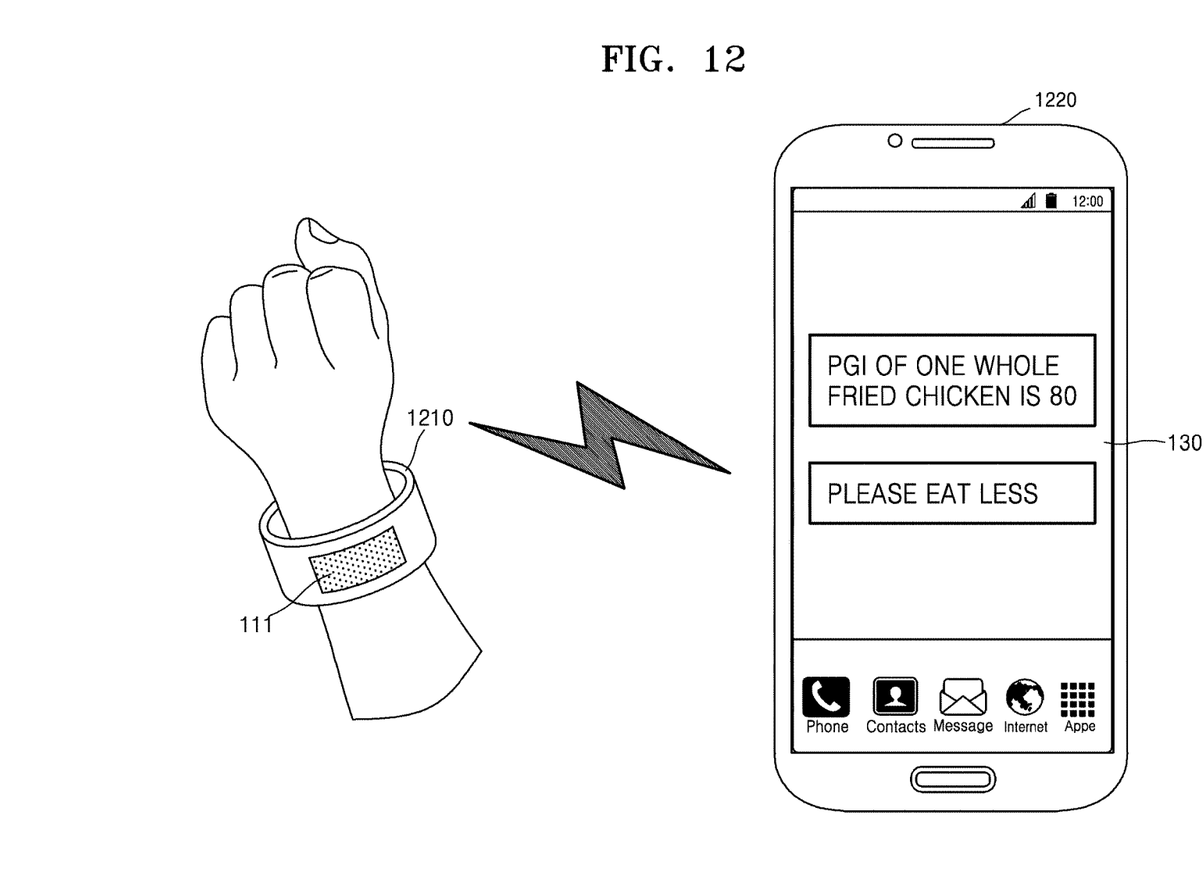
FIG. 12 is a diagram of a slave and a master, according to an exemplary embodiment.

FIG. 12 is a diagram of a slave 1210 and a master 1220, according to an exemplary embodiment. The sensor 111 for detecting biomedical information is arranged in the slave 1210, and the display 130 is arranged in the master 1220.

The slave 1210 may be a wearable device that may be worn by a user. For example, the slave 1210 may be a wrist type device that may be detachably worn on the wrist of a user. The master 1220 may be mobile phones, smartphones, desktop computers, laptop computers, tablet PCs, e-book terminals, digital broadcasting terminals, personal digital assistants (PDAs), internet protocol televisions (IPTVs), digital televisions (DTVs), servers for managing health, etc., but the exemplary embodiments are not limited thereto.

In addition, the exemplary embodiments may also be implemented through computer-readable code and/or instructions on a medium, e.g., a non-transitory computer-readable medium, to control at least one processing element to implement any above-described embodiments. The medium may correspond to any medium or media which may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to one or more exemplary embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

The foregoing exemplary embodiments and advantages are merely exemplary embodiments and are not to be construed as limiting the exemplary embodiments. The exemplary embodiments can be readily applied to other types of devices. Also, the description of the exemplary embodiments is intended to be illustrative, and not to limit the scope of the claims, and many alternatives, modifications, and variations will be apparent to those skilled in the art.

What is claimed is:

1. A method of operating a health care apparatus, the method comprising:
   generating, by a processor, a first blood glucose pattern of an examinee that indicates a blood glucose level of the examinee over a first period of time;
   generating, by a processor, a second blood glucose pattern of the examinee that indicates the blood glucose level of the examinee over a second period of time;
   generating, by the processor, a third blood glucose pattern of the examinee that indicates the blood glucose level of the examinee over a third period of time;
   calculating, by a processor, a glycemic index of the examinee, based on the first blood glucose pattern, the second blood glucose pattern, and the third blood glucose pattern;
   detecting, by the processor, biomedical information other than the blood glucose level of the examinee;
   calculating, by the processor, a degree of correlation between the glycemic index and the biomedical information;
   determining, by the processor, whether the degree of correlation is greater than or equal to a value and whether the glycemic index is within a range; and
   monitoring, by the processor, the biomedical information, in response to the degree of correlation being determined to be greater than or equal to the value and that the glycemic index being determined to be within the range.

2. The method of claim 1, wherein the generating the first blood glucose pattern, the second blood glucose pattern, and the third blood glucose pattern comprises detecting the blood glucose level in a non-invasive manner.

3. The method of claim 2, wherein the detecting comprises using at least one among Raman spectroscopy, infrared absorption spectroscopy, and a radio frequency analysis method.

4. The method of claim 1, wherein the examinee has an empty stomach during the first period of time.

5. The method of claim 1, wherein the second period of time is after the examinee ingests a first meal, and
the third period of time is after the examinee ingests a second meal.

6. The method of claim 5, wherein the first meal is a standard meal that is set by the examinee, and
the second meal is a current meal that is input by the examinee.

7. The method of claim 1, wherein the first period of time, the second period of time, and the third period of time have a same duration.

8. The method of claim 7, wherein the same duration is less than or equal to 24 hours.

9. The method of claim 1, wherein the calculating comprises:
calculating a first blood glucose area by integrating a first difference between the second blood glucose pattern and the first blood glucose pattern with respect to time;
calculating a second blood glucose area by integrating a second difference between the third blood glucose pattern and the first blood glucose pattern with respect to time; and
calculating the glycemic index, based on the first blood glucose area and the second blood glucose area.

10. The method of claim 9, wherein the glycemic index is a ratio of the second blood glucose area to the first blood glucose area.

11. The method of claim 1, further comprising displaying the glycemic index.

12. The method of claim 11, wherein the glycemic index is displayed as at least one among a figure and a graph.

13. The method of claim 1, further comprising:
determining an amount of exercise that is performed by the examinee; and
calculating a degree of correlation between the glycemic index and the amount of exercise.

14. A method of operating a health care apparatus, the method comprising:
generating a first blood glucose pattern of an examinee that indicates a blood glucose level of the examinee over a first period of time;
generating a second blood glucose pattern of the examinee that indicates the blood glucose level of the examinee over a second period of time;
generating a third blood glucose pattern of the examinee that indicates the blood glucose level of the examinee over a third period of time;
calculating a glycemic index of the examinee, based on the first blood glucose pattern, the second blood glucose pattern, and the third blood glucose pattern;
determining an amount of exercise that is performed by the examinee;
calculating a degree of correlation between the glycemic index and the amount of exercise;
determining whether the degree of correlation is greater than or equal to a value and whether the glycemic index is within a range; and
instructing the examinee to exercise, in response to the degree of correlation being determined to be greater than or equal to the value and the glycemic index being determined to be within the range.

15. A health care apparatus comprising:
a processor configured to:
generate a first blood glucose pattern of an examinee that indicates a blood glucose level of the examinee over a first period of time;
generate a second blood glucose pattern of the examinee that indicates the blood glucose level of the examinee over a second period of time;
generate a third blood glucose pattern of the examinee that indicates the blood glucose level of the examinee over a third period of time; and
calculate a glycemic index of the examinee, based on the first blood glucose pattern, the second blood glucose pattern, and the third blood glucose pattern;
detect biomedical information other than the blood glucose level of the examinee;
calculate a degree of correlation between the glycemic index and the biomedical information;
determine whether the degree of correlation is greater than or equal to a value and whether the glycerine index is within a range; and
monitor the biomedical information, in response to the degree of correlation being determined to be greater than or equal to the value and the glycemic index being determined to be within the range.

16. The apparatus of claim 15, further comprising a sensor configured to detect the blood glucose level.

17. The apparatus of claim 15, wherein the examinee has an empty stomach during the first period of time,
the second period of time is after the examinee ingests a first meal, and
the third period of time is after the examinee ingests a second meal.

18. The apparatus of claim 15, wherein the first period of time, the second period of time, and the third period of time have a same duration.

* * * * *